United States Patent
Hamid et al.

(10) Patent No.: US 9,446,434 B2
(45) Date of Patent: Sep. 20, 2016

(54) INSPECTION APPARATUS AND METHOD USING PATTERN RECOGNITION

(75) Inventors: Gabriel Hamid, Loughton (GB); Charles Dean Mallah, Hampton (GB)

(73) Assignee: BUHLER SORTEX LTD., London (GB)

( * ) Notice: Subject to any disclaimer, the term of this patent is extended or adjusted under 35 U.S.C. 154(b) by 799 days.

(21) Appl. No.: 13/384,062

(22) PCT Filed: Jul. 5, 2010

(86) PCT No.: PCT/GB2010/001290
§ 371 (c)(1),
(2), (4) Date: Apr. 16, 2012

(87) PCT Pub. No.: WO2011/007117
PCT Pub. Date: Jan. 20, 2011

(65) Prior Publication Data
US 2012/0188363 A1     Jul. 26, 2012

(30) Foreign Application Priority Data

Jul. 16, 2009  (GB) .................................. 0912390.2

(51) Int. Cl.
*H04N 7/18* (2006.01)
*B07C 5/342* (2006.01)
(Continued)

(52) U.S. Cl.
CPC ......... *B07C 5/3422* (2013.01); *G01N 21/8851* (2013.01); *G01N 21/85* (2013.01)

(58) Field of Classification Search
CPC .. G01N 21/88; G01N 21/8803; G01N 21/89; G01N 21/8903
USPC ............................................ 348/88; 349/141
See application file for complete search history.

(56) References Cited

U.S. PATENT DOCUMENTS 5,377,279 A * 12/1994 Hanafusa et al. ............ 382/141
5,692,621 A    12/1997 Davis et al.
(Continued)

FOREIGN PATENT DOCUMENTS

CN     1288156 A    3/2001
CN     1691990 A    11/2005
(Continued)

OTHER PUBLICATIONS

PCT International Bureau, Notification Concerning Transmittal of International Preliminary Report on Patentability and Report, in International application No. PCT/GB2010/001290, dated Jan. 26, 2012. (7 pages).

*Primary Examiner* — Mohammed Rahaman
*Assistant Examiner* — Jimmy S Lee
(74) *Attorney, Agent, or Firm* — McAndrews, Held & Malloy, Ltd.

(57) ABSTRACT

Inspection apparatus comprises a feed system for delivering a stream of articles to an imaging zone. A camera generates image data from the stream at the imaging zone for processing by a computer. The computer comprises a pattern recognition system for identifying defects in areas from the image data, and for ranking identified defects. The pattern recognition system is programmed to operate according to multiple defect criteria. The computer is also coupled to a graphical user interface to display the areas identified from the image data as thumbnails on the interface arranged according to rank of the identified defects in the areas, in each of at least two defect criteria. The areas from the generated image data will normally be defined around each identified defect with the defect central therein. These areas, or thumbnails, can overlap.

15 Claims, 7 Drawing Sheets

(51) Int. Cl.
*G01N 21/88* (2006.01)
*G01N 21/85* (2006.01)

(56) References Cited

U.S. PATENT DOCUMENTS

| | | | |
|---|---|---|---|
| 5,887,073 A * | 3/1999 | Fazzari et al. | 382/110 |
| 6,124,560 A | 9/2000 | Roos et al. | |
| 6,266,437 B1 * | 7/2001 | Eichel et al. | 382/149 |
| 6,944,342 B1 * | 9/2005 | Stahl et al. | 382/224 |
| 7,522,664 B1 * | 4/2009 | Bhaskar et al. | 375/240.01 |
| 7,968,814 B2 * | 6/2011 | Imai et al. | 209/580 |
| 2004/0032979 A1 | 2/2004 | Honda et al. | |
| 2005/0105767 A1 | 5/2005 | Rosenbaum | |
| 2006/0109454 A1 * | 5/2006 | Engelbart et al. | 356/237.1 |
| 2009/0050540 A1 * | 2/2009 | Imai et al. | 209/580 |

FOREIGN PATENT DOCUMENTS

| | | |
|---|---|---|
| EP | 1083007 A2 | 3/2001 |
| GB | 2452164 A | 2/2009 |
| GB | 2452164 A | 2/2009 |
| JP | 2000146847 | 5/2000 |
| JP | 2002312762 | 10/2002 |
| JP | 2006198539 | 1/2005 |
| JP | 2005074412 | 3/2005 |
| JP | 2006513402 | 4/2006 |
| JP | 2007225351 | 6/2007 |
| JP | 2009050760 | 3/2009 |

* cited by examiner

| Thumbnail | Sorting Criterion 1 "Spot Sorting" | Sorting Criterion 2 "Colour Sorting" |
|---|---|---|
| A | 42 | 66 |
| B | - | 67 |
| C | 44 | 68 |
| D | - | 68 |
| E | 42 | 69 |
| F | - | 69 |
| G | - | 69 |
| H | 43 | 70 |
| I | 43 | 71 |
| J | 44 | 70 |
| K | - | 70 |
| L | 46 | 70 |
| M | - | 71 |
| N | 45 | - |
| O | 45 | - |
| P | 48 | 72 |
| Q | 46 | - |
| R | 47 | - |

Fig. 11
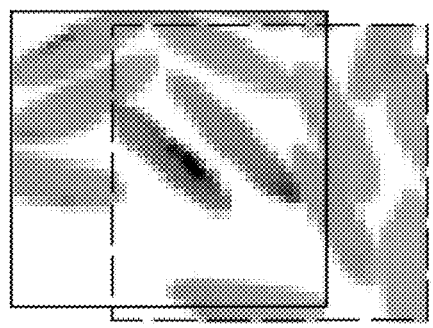
Fig. 12
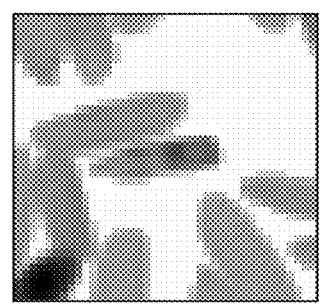
Fig. 13

INSPECTION APPARATUS AND METHOD USING PATTERN RECOGNITION

This application is a 371 National Phase filing of International Patent Application Serial No. PCT/GB2010/001290 filed Jul, 5, 2010, which claims priority benefit of EP Patent Application Serial No. 0912390.2 filed Jul. 16, 2009. Both applications are incorporated herein by reference in their entirety.

This invention relates to optical sorting machines, particularly for sorting bulk foodstuffs such as grain, rice, nuts, pulses, fruit and vegetables. Examples of such apparatus are described in International Patent Specification No. WO98/018574 and European Patent Specification No. 0 838 274, the disclosures whereof are hereby incorporated by reference. In machines of this type a stream of particles to be sorted is delivered in free flight to a sorting zone where articles to be removed are rejected by blasts of gas, normally air, from ejectors disposed adjacent the flight path. In such machines the required throughput is normally determined by the production rates elsewhere in a processing plant. Normally though, the required throughput is high, and measured in tonnes per hour.

Reference is also directed to our International Patent Application filed today entitled "Defect Viewer for Sorting Machines", based on British Application No: 9012388.6, the disclosure whereof is incorporated by reference.

Food producers use optical sorting machines to remove defects from the product stream so that the sorted product meets an agreed grade or quality standard, whilst maximising the total production yield. The quality standard usually specifies individual maximum levels of contamination for different types of defects. For example, in sorting rice the defects might be insect-damaged peck-grains, chalky grains and yellow grains, with maximum levels for these three contaminants, say: <0.1% peck, <1% chalky and <0.2% yellow. Hence, in order to optimise the total yield the operator aims to set-up the sorting apparatus so that the sorted rice has concentrations of these contaminants just below the maximum permissible levels. As used herein, the term "defect" should be understood to include blemishes on articles being sorted and whole articles which are unsatisfactory for this or another reason, and includes foreign material or extraneous product.

Optical sorting machines identify defects in the product being sorted by using known techniques for continuously creating images of product in the stream at an imaging zone; and instructing the ejectors in accordance with defects identified in the images. Usually, each sorting criterion is targeted at a different type of defect. However, a specific sorting criterion may detect another type of defect, either because an article has more than one type of defect or because the sorting criteria are not wholly independent. For example, a sorting criterion for rice, designed to detect peck-grains may also identify some chalky and some yellow grains for removal. Furthermore, even though a particular criterion will typically identify the majority of one type of defect, it will also incorrectly classify some good product as defect. As the sensitivity of the sorting criterion is increased, more defects are removed. However, this is likely also to increase the proportion of good product that is removed.

Another factor that results in the unintentional removal of good product from the product stream is the density of the product in stream. At a reasonable throughput, a defective item is commonly surrounded by good product, and the action of the ejector does not achieve a perfect separation. In other words, when aiming at a defect acceptable articles are removed with the defective article. This can be the case even if the size of the ejector nozzle is smaller than the size of the articles being sorted. In order to ensure a defective article is rejected, the size of the gas blast, or the area of its intersection with the product stream, is extended to account for uncertainties in both the position and velocity of the defective article. This area can be extended by firing multiple ejectors simultaneously and/or extending the duration of the gas blast. The ejectors are normally disposed in an array extending laterally across one side of the product stream, so the area of intersection of the gas with the stream in such an arrangement is extended laterally by firing multiple ejectors, and longitudinally by extending the duration of the gas blast.

The above issues make it hard for an operator to optimise the setup of an individual sorting apparatus. It is not always clear which sorting criterion or criteria to adjust and if so, which parameters to alter and by how much, or whether to adjust the size of the area of intersection of gas blast with the product stream. The present invention seeks to facilitate such operation.

In the field of Computer Vision, it is a well-known technique to "back-project" the output of a Pattern Recognition System onto the original image data. For example, European Patent Specification No: 0645727 A2, incorporated by reference, describes an apparatus for highlighting (back-projecting) the areas in an x-ray image that have been identified by a computer-aided diagnostic system as suspected abnormalities.

It is also well-known within the field of Computer Vision, that a simple yet effective technique to fine-tune a pattern recognition system is to provide the operator with visual feedback of this back-projected data whilst one or more parameters of the pattern recognition system are adjusted; for example "Skin-Tool" described in the paper by M. Jones and J. Rehg in IEEE Computer Society Conference on Computer Vision and Pattern Recognition, 1999, Volume 1, pages 1-280, incorporated by reference.

A pattern recognition system typically includes a feature extractor for extracting information, and a classifier for processing such information according to a given criterion. Such systems are described in U.S. Pat. Nos. 3,636,513 and 3,638,188, incorporated by reference.

In many industrial inspection and sorting tasks, there is often more than one type of defect. A well-known technique to aid the operator to fine-tune the identification of defects in such a case, is to display the images of the detected defects arranged in groups according to type, for example U.S. Pat. No. 7,424,146, incorporated by reference, describes a graphical user interface which enables the operator to change one or more parameters and displays the subsequent change to the membership of the different groups.

In many sorting applications the required throughput is a given, and the trade-off is between quality and yield. US Patent Application 2005/0273720 A1, incorporated by reference, describes a utility for storing image data from a batch of production and enabling the operator to see what would be the effect of varying one or more parameters of the pattern recognition system in terms of the characteristics of defects identified (i.e. quality control) and the number of items rejected (i.e. yield).

In the field of food sorting machinery, British Patent Specification No: 2,452,164A and U.S. Pat. No. 7,298,870, incorporated by reference, describe a graphical user interface for adjusting the thresholds of one or more sorting criteria whilst the operator views a display of a stored image, highlighting the position of the detected defects combined with the contour of the defective grain, and highlighting which ejectors fire at the grain.

The present invention is directed at inspection apparatus that can be part of a sorting machine of the kind described above, or be used separately in the analysis of a product stream. The apparatus comprises a feed system for delivering a stream of articles to an imaging zone, and a camera for generating image data at the imaging zone. A computer processes image data from the camera. According to the invention, the computer comprises a pattern recognition system for identifying defects in areas from the image data and for ranking identified defects, the system being programmed to operate according to multiple defect criteria. The computer is coupled to a graphical user interface to display the areas from the image data as sub-images or thumbnails on the interface and arranged according to rank of the identified defects in the areas in each of at least two defect criteria. The areas from the generated image data will normally be defined around each identified defect with the defect central therein. These areas, or thumbnails, can overlap.

In one embodiment of the invention this pattern recognition system comprises a feature extractor for extracting information from the image data, and a classifier for interpreting such information. Such a system can be used when one of the defect criteria is the shape or size and the thumbnail with a defect according to shape includes a silhouette of the respective defect or article.

The computer in apparatus of the invention is normally programmed with a sensitivity level defining a qualifying ranking in each criterion, and to display said images in sequence with the qualifying rankings at the same level in the display. Normally the thumbnail derived from an article exhibiting defects in more than one criterion is displayed only in the sequence in which its rank is lower than it is in the at least one other criterion relative to its qualifying ranking. At least one of the sensitivity levels is preferably variable.

Apparatus according to the invention may be operated in such a way that the display on the graphical user interface includes thumbnails that do not exhibit defects. This can be accomplished by adjusting the sensitivity levels such that every article in the stream effectively constitutes or bears a defect. Apparatus in which the computer is programmed with sensitivity levels defining qualifying rankings may also be operated in such a way that the display on the interface shows only thumbnails with defects ranked below the qualifying rankings.

The present invention also includes modifications of the apparatus described above adapted to inspect webs of material for blemishes or other features perceptible by the camera. The feed system would of course be different, and the pattern recognition system adapted to identify defects on the web for display in thumbnails on the graphical user interface.

In apparatus according to the invention the computer will normally generate and process image data from the stream of articles without creating a visible image. However, the computer can also be coupled to the or another graphical user interface to generate such a visible image.

Apparatus according to the invention can be adapted to perform as a sorting machine by including a sorting zone downstream of the imaging zone, and ejectors at the sorting zone for selectively ejecting articles from the stream, typically by discharging gas (normally air) in pulses. The defect criteria are sorting criteria; and the computer is adapted to process image data from the camera and instruct the ejectors according to the sorting criteria. Preferably, the sorting criteria comprise at least two of spot sorting, colour sorting, size sorting and shape sorting.

In sorting apparatus using the present invention the pattern recognition system typically comprises a colour classifier for identifying pixels corresponding to potential defects in a said stream of articles and a spatial filter for determining whether the identified potential defect pixels warrant ejection of a respective article. Potential defects and potential defect pixels that warrant ejection of respective articles can be highlighted separately on the displayed image.

As does the apparatus described in our co-pending Application filed today and referred to above, apparatus of the present invention also enables an estimation to be made of the proportion of rejected articles relative to the totality of articles in the stream. The image data is analysed by the computer to identify pixels in the stream image which correspond to articles in the product stream, whether defective or not. The computer is adapted to calculate the number of such pixels in the image data of articles to be ejected, relative to the total number of such pixels as an estimate of the proportion of articles in the stream that are being rejected. While such a calculation from any stream image is of course specific to that image, a succession of such calculations will provide a useful guide to the proportion of product being rejected in the product stream as a whole. These proportions, as percentages, can be displayed on the interface adjacent a column of ranked thumbnails adjacent each sensitivity setting for one criterion or a combination of criteria.

The above and other features and advantages of the present invention will be apparent from the following description of a preferred embodiment given by way of example only, in which reference will be made to the accompanying schematic drawings. In the drawings.

FIG. 9 lists the ranking of defects in a range of thumbnails from a stream image according to two different sorting criteria;

Figures 10A, 10B:
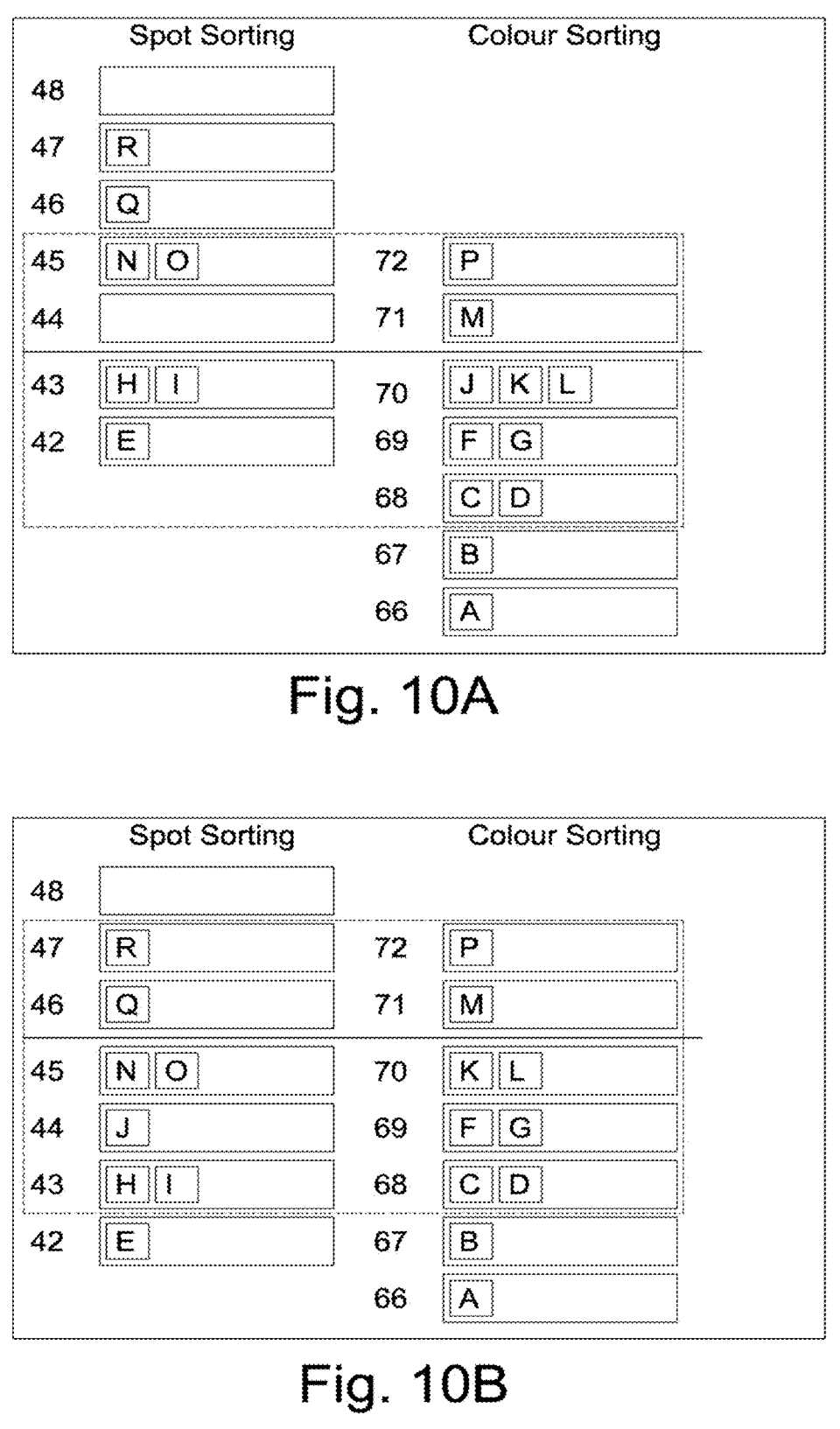

FIGS. 10a and 10b illustrate how alteration of sensitivity alters the overall ranking of a defect;

FIG. 11 illustrates how thumbnails can be ranked according to the shape of an article therein;

FIG. 12 illustrates two overlapping thumbnails; and

FIG. 13 illustrates a thumbnail with an additional severe defect shown.

Figure 1:
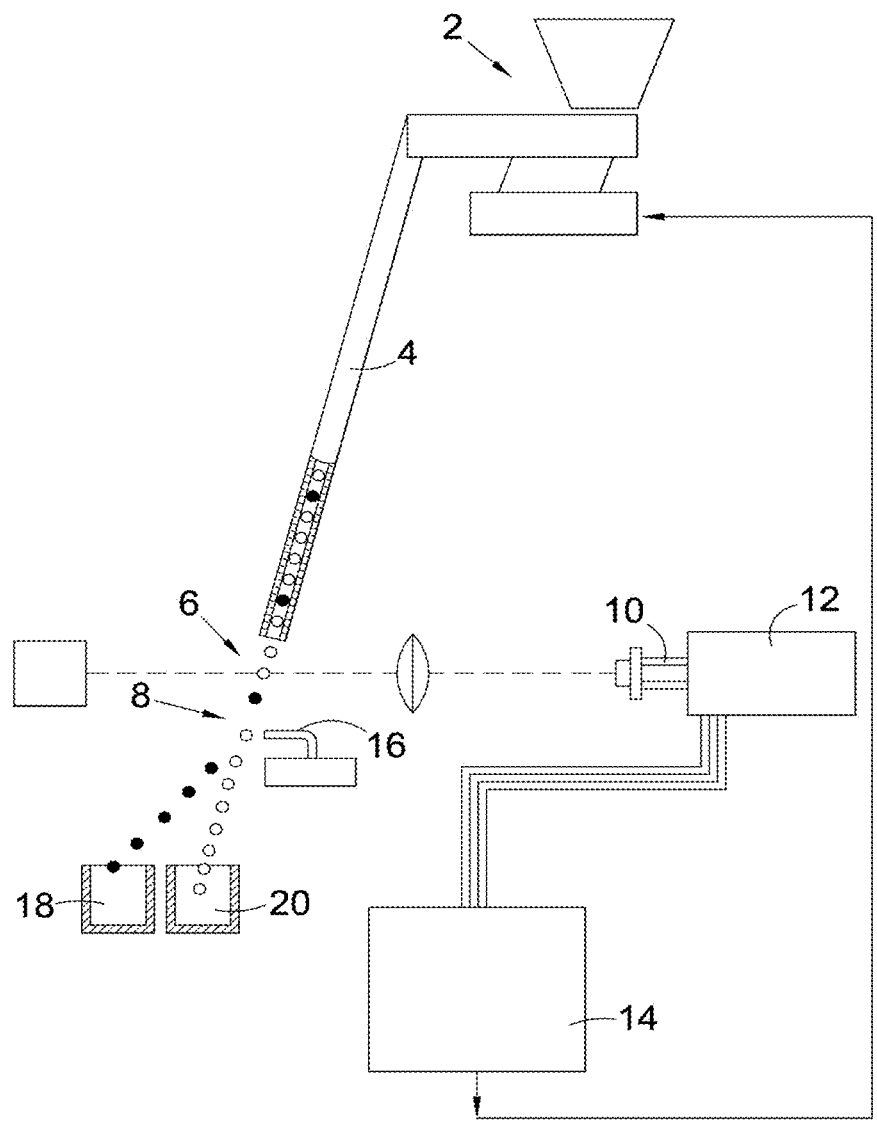
FIG. 1 is a side view of an optical sorting machine of the kind disclosed in our International Patent Specification No: WO2004/024350.

As shown in FIG. 1, optical apparatus of the kind to which this invention relates has a feed mechanism comprising an infeed hopper assembly 2 and chute 4 for delivering a stream of articles to be sorted through an imaging zone 6 to a sorting zone 8. Line-scan cameras 10 generate image data from the imaging zone which passes to a computer 12 coupled to a graphical user interface 14. The computer 12 processes the image data to identify articles in the product stream to be removed, and so instructs an array 16 of ejectors to discharge pulses of air at the stream to deflect selected articles from the stream to a reject hopper 18. Product remaining in the stream continues into accept hopper 20. This manner of rejecting poor quality articles from a product stream is well known in the food processing industry. The line-scan cameras can be either visible or infra-red, ultra violet, X-ray, monochromatic or polychromatic.

The criterion or criteria that determine whether an article in the product stream bearing a particular defect is to be removed can be one or more of several alternatives, four of which are size, shape, spot and colour. The operator can control the performance of the apparatus by altering the defect parameters of the sorting criteria. The aim of the present invention is to provide the operator with useful guidance as to what such adjustments can or should be made.

Figure 2:
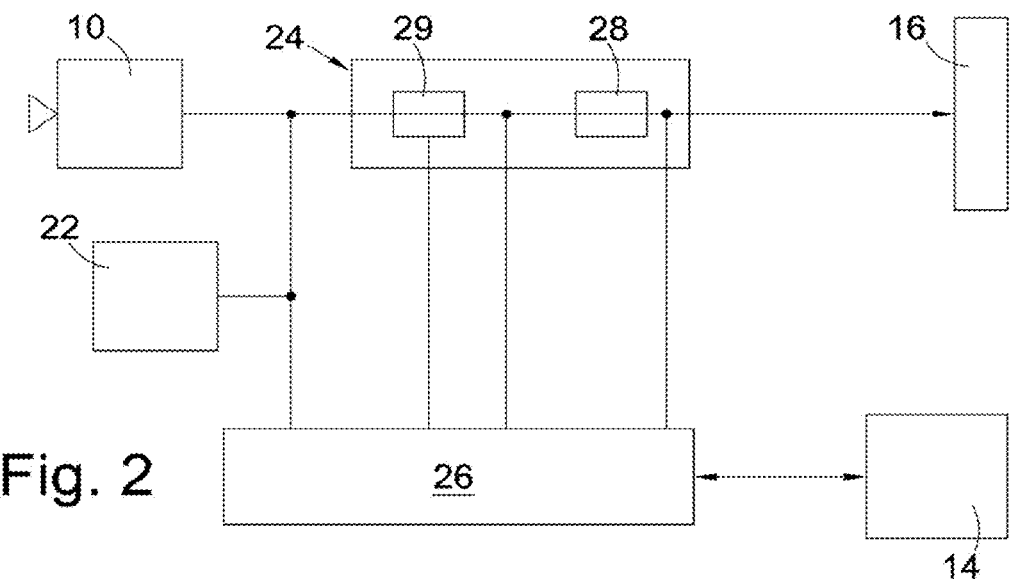
FIG. 2 illustrates details of the computer processing operation.

FIG. 2 illustrates some details of the computer 12 in FIG. 1. It includes a memory 22, a processor 24 and a system controller 26. The processor 24 includes a pattern recognition system 29, and is adapted to apply a set of sorting criteria to image data received from the camera 10, for the purpose of detecting the location of defects. The processor also includes a selector 28 for generating the appropriate ejector data, and instructing the ejectors 16. The pattern recognition system 29 and the selector 28 operate according to defect parameters and ejection parameters respectively. These parameters are set by the system controller 26. Data generated at each stage of the processor 24 is passed to the system controller 26. In turn, the system controller 26 passes data to and from the graphical user interface 14. The operator of the apparatus can make adjustments to the defect parameters and the ejection parameters at the graphical user interface 14. The operator makes these adjustments in response to information provided at the graphical user interface 14.

A sorting criterion is implemented in two basic stages, namely a feature extractor and a classifier. The performance of each sorting criterion is governed by a number of defect parameters, one of which is usually a sensitivity parameter. Sensitivity is typically expressed as a percentage where 0% corresponds to little or no defects and 100% corresponds to many or all defects detected. Both the feature extractor and the classifier may have defect parameters, and the sensitivity parameter may be associated with either the feature extractor or the classifier. The feature extractor computes a feature-based representation of the image data. The classifier identifies the defects from this feature data.

Figure 3:
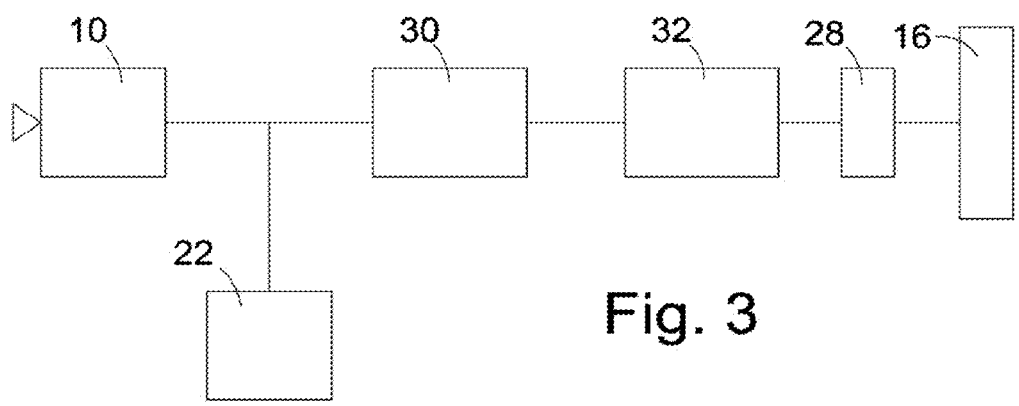
FIG. 3 shows details of a particular pattern recognition system.

FIG. 3 illustrates a pattern recognition system using a colour sorting criterion. The image data passes to a colour classifier 30 which performs the initial extraction step and identifies whether each piece of image data or pixel belongs to a specified set of defect colours. The output from the colour classifier, called classified data, identifies which pixels correspond to potential defects. For monochromatic image data, the preferred colour classification is accomplished by applying a first threshold on the pixel intensity. The defect parameter that sets this threshold is the sensitivity of that sorting criterion. For polychromatic image data, the preferred colour classifier is a decision boundary in the multi-dimensional colour space. The defect parameter which controls the position of this decision boundary is the sensitivity for that sorting criterion.

The classified data passes to the spatial filter 32. The spatial filter filters the classified data according to size; ie, the number of classified pixels within a local neighbourhood on the image. The size of the spatial filter and the size of the local neighbourhood are defect parameters of the spatial filter. The output signal from this stage is the colour defect data that indicates which pixels correspond to defects. A spot sorting criterion is similar to a colour sorting criterion except that the size of the spatial filter is set to one pixel.

In size sorting of articles, the extracted feature is typically the area of an article and the classifier is a threshold on the size of the article. In this case, there is only one defect parameter; namely the sensitivity adjustment that determines the size threshold. The size sorting of articles relies upon the throughput of the product stream to be sufficiently low so that the individual articles can be seen separate from one another. In shape sorting, the feature extractor extracts shape features of an article or part of an article to form a shape feature vector. The classifier identifies each article or part of an article as either accept or defect on the basis of its shape feature vector. Both the feature extractor and the classifier may have many defect parameters. The sensitivity of the shape sorting criterion controls the position of the decision boundary of the classifier.

The pattern recognition system 29 in the processor 24 may operate according to many separate sorting criteria generating different defect data for the selector 28. All the defect data is combined to generate instructions for the ejectors 16. The preferred means of combining the defect data is a simple OR device. In other words, if any sorting criterion decides a pixel corresponds to a defect, then the ejectors 16 must be instructed with regard to that pixel.

In generating instructions for the ejectors, the defect data is filtered and extended both laterally and in the direction of flow of the product stream. The preferred mechanism for extending the area of intersection of gas blasts from the ejectors is to include a first ejection parameter that provides an option for activating adjacent ejectors, and a second ejection parameter that specifies the duration of each gas blast from each ejector. This duration is normally defined in integral multiples of the time taken to capture one scan line of data from the camera.

Figure 4:
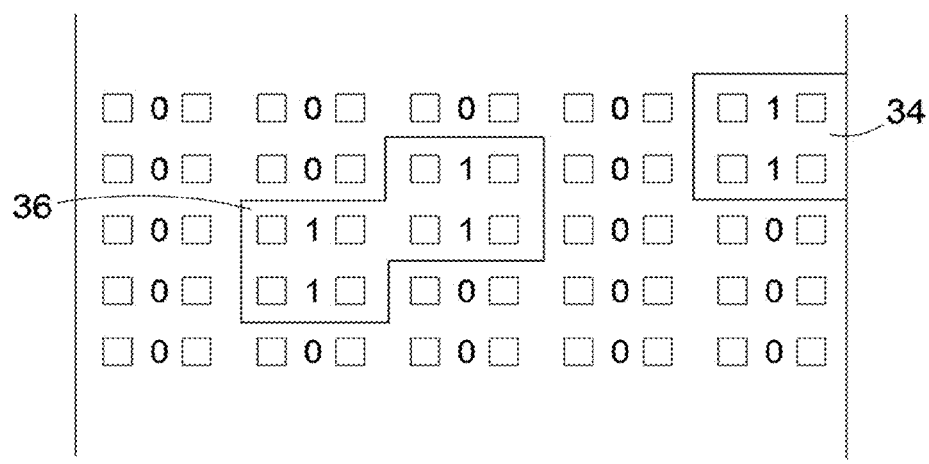
FIG. 4 shows a portion of the graphical user interface illustrating two areas of intersection of a gas pulse with the product stream.

The graphical user interface 14 displays an image of the product stream at the imaging zone. A section from such an image is shown in FIG. 4 which, for ease of illustration, is of an arrangement in which there are twice as many pixels as ejectors. The preferred image resolution is normally much higher than the ejector resolution, for example by a multiplication factor of sixteen. The defect data is scaled down to the resolution of the ejectors. In the case illustrated, the resulting ejector data is a Boolean signal per ejector per scan line indicating the ejector state; on or off as indicated in the Figure as "1" or "0". These will of course not appear in the displayed image.

During normal sorting, the instruction to an ejector is delayed to allow for the time taken for the selected article in a product stream to flow from the line of sight of camera 10 to the line of fire of the ejectors 16, and the time taken for the gas blast to reach the article from the ejector.

For fine tuning of the apparatus, the operator selects a diagnostic mode of operation. A snapshot image of a section of the product stream at the imaging zone is captured to the memory 22. The image is analysed in the same way as is the image data in normal running of the apparatus, but it is preferred to duplicate the respective hardware and software so that the normal sorting can continue while the operator views the machine diagnostics and considers what might occur as a consequence of altering the ejection and defect parameters.

Figure 5:
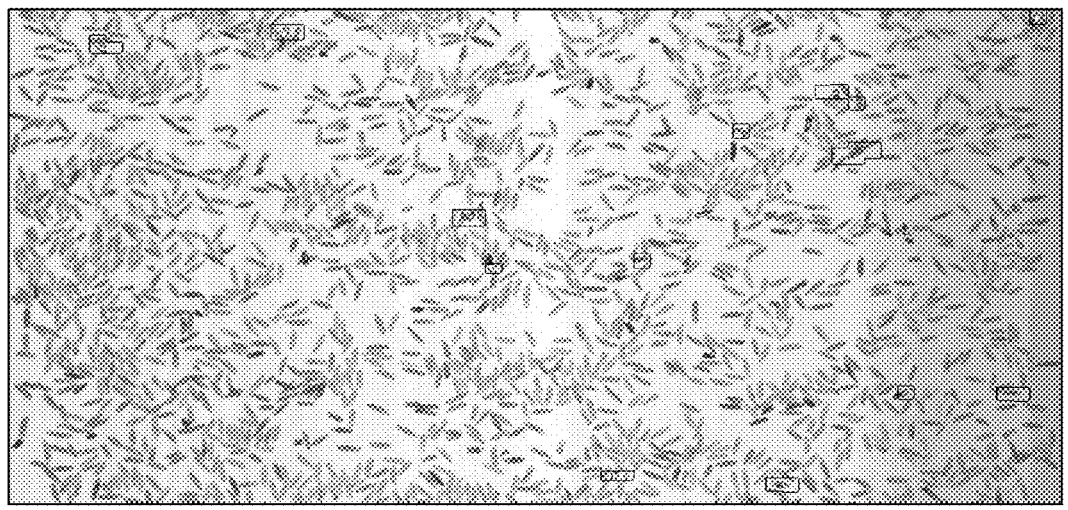
FIG. 5 illustrates a display image of a product stream as it is shown by the graphical user interface.

The graphical user interface 14 has four diagnostic facilities; a defect viewer; a "Rogues' Gallery"; a percentage reject estimation; and a defect browser. Using the defect viewer facility, the interface displays the image and highlights on the displayed image the areas of intersection of air pulses from the ejectors with the product stream, as illustrated in FIG. 5. This is illustrated in FIG. 4 in the two zones indicated. In zone 34 one ejector having a spread of two pixels is fired over a period comprising two scan lines. In zone 36 two zones each similar to zone 34 are adjacent with one ejector being fired for a period corresponding to two scan lines, with an adjacent ejector being activated for a similar period started halfway through the duration of the earlier fired ejector.

The defect viewer facility on the interface can indicate the pixels corresponding to both the classified data and the defect data. Where a number of different colour sorting criteria are used, this can be accomplished by highlighting the respective pixels with a distinctive colour. The preferred colour scheme is to use a different hue for each sorting criterion, with saturated colour for defect pixels and unsaturated colour (ie, paler) for the classified pixels. The defect viewer facility provides the option to switch between the pixels identified in each sorting criterion. The facility also provides for adjusting the respective defect parameters with the consequence that the image data stored in the memory is reanalysed, and the displayed image correspondingly altered. In this way, the operator can see the overall effect of any parameter change in a single snapshot image.

The defect viewer facility enables the operator to adjust the size of the area of intersection of the ejector blast with the product stream by adjusting the ejection parameters. The operator can very quickly see which sorting criteria have triggered which ejector blasts, and if the area boundary encompasses part of the displayed image that appears to be good product, then the operator knows which criterion or criteria needs or need adjustment. Similarly, if a highlighted classified pixel that suggests the presence of a defect is not within an area of intersection, then the operator knows that increasing the sensitivity of the respective sorting criterion should result in such defective articles being ejected.

As discussed below, defects can be ranked according to severity. The sorting machine can adjust the size of the area of intersection of the ejector blast according to the severity of a defect. This may be desirable to ensure the ejection of a severely defective article from the product stream. Any such variation will be identified in the displayed image. The size of the area of intersection can be directly related to the severity of the defect, and be determined automatically by the machine. The relationship may also be adjusted by the machine operator.

In order to see the net effect on a large sample of product, the operator can repeat the capture and analysis of multiple images. The memory can store all images captured, and if desired these images can be of contiguous sections of the product stream enabling the operator to scroll along a section of the stream in the conduct of this analysis.

Figure 6:
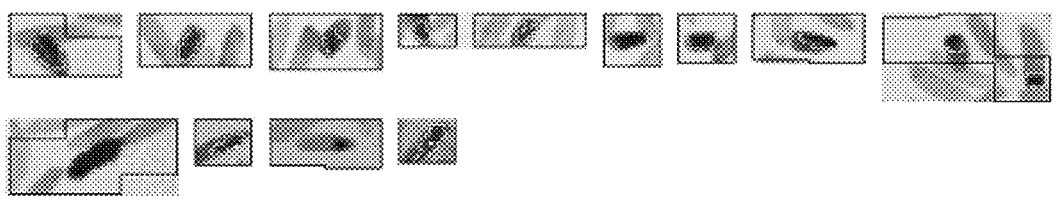
FIG. 6 illustrates a gallery of patches extracted from the display image of FIG. 5.

The second diagnostic facility provided on the graphical user interface is the "Rogues' Gallery". This is assembled by extracting from the stream image on the interface the intersection areas, and displaying them in a separate screen for inspection. For ease of identification and presentation, the boundary of each area is resolved into a square or rectangular patch, and each patch is then displayed. The manner in which a patch is defined is illustrated in FIG. 6, which shows the respective areas from the representation of FIG. 5 assembled within patches in a gallery. The edge of each connected region of homogeneous classified data is highlighted on each patch as shown in FIG. 6. It will be appreciated that the gallery of FIG. 6 can be extended to include patches from different and/or sequential images of product stream sections, and each patch can of course be labelled with the sorting criteria that has resulted in its selection. The gallery of patches provides a ready indication of the nature of defects being identified and again, useful information for the operator in controlling the sorting process.

It will be appreciated from the information that is being assembled that an estimation of the proportion of reject articles in a product stream based on a single one of or a plurality of stream images of the kind described above can be calculated. Data in the memory 22 can again be analysed to identify every pixel in the image as corresponding to either the presence or the absence of an article. This can be readily accomplished using known techniques from both monochromatic and polychromatic image data. The percentage of reject can then be estimated as the number of pixels that correspond to articles in areas of intersection of ejection gas with the product stream relative to the number of pixels that correspond to the totality of articles in the stream image. This estimation can of course be recalculated each time the operator makes an adjustment to either the defect or ejection parameters.

The fourth diagnostic facility provided by the graphical user interface is the defect browser. The defect browser extracts sub-images or thumbnails from image data stored in memory 22, and ranks each thumbnail according to a respective sorting criterion. The rank of a thumbnail is the lowest sensitivity of that sorting criterion at which it would be first rejected. That sensitivity can be obtained by sweeping over the range of sensitivities in turn for each sorting criterion, while all other defect parameters remain at the values set on the sorting machine. However, for some criteria such a sweep may not be necessary. It then arranges the thumbnails in rank order. The process is most simply understood when each extracted thumbnail encompasses one and only one article from the product stream, which is only feasible when the product throughput is relatively low. In those circumstances, individual articles can be identified and thumbnail images extracted from the image data, even though the thumbnails may not necessarily be square.

In most optical sorting machines the throughput is so high that it is not feasible to identify individual objects with accuracy. To accommodate this, in the defect browser facility in the apparatus described thumbnails all having the same size and shape are extracted by centering a thumbnail around each region of interest in the displayed image. The regions of interest can be detected by increasing the sensitivity of each sorting criterion in turn, and merging all the resulting defect data to form the regions of interest. We shall first consider the situation in which the thumbnails do not overlap.

Figure 7:
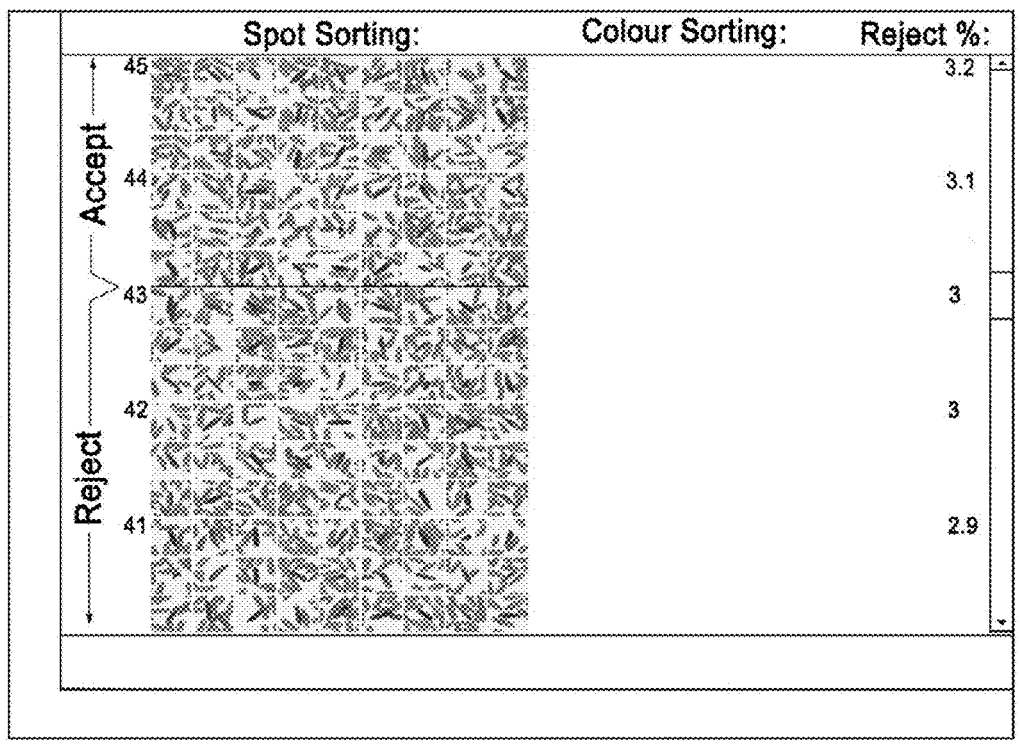
FIG. 7 shows a rearrangement of thumbnails from the stream image relative to a single sorting criterion.

FIG. 7 illustrates the displayed image on the graphical user interface using the defect browser facility with the thumbnails arranged in accordance with just one sorting criterion; in this case spot sorting. This is presented in a single column divided into rows corresponding to a particular sensitivity setting for this criterion. In FIG. 7 the thumbnails are displayed in groups according to the sensitivity at which they would be first rejected by the sorting criterion.

Across the centre of the display is a bold horizontal line that marks the current setting for sensitivity. All the thumbnails below this line are notionally rejected, and all the thumbnails above the line are notionally accepted. The defect browser facility includes a control for adjusting this sensitivity setting. Such adjustment shifts the rows relative to this line. The interface is not large enough to show all the rows corresponding to all the available sensitivity settings, so provision is normally made to scroll for an extended or the entire range of settings.

Figure 8:
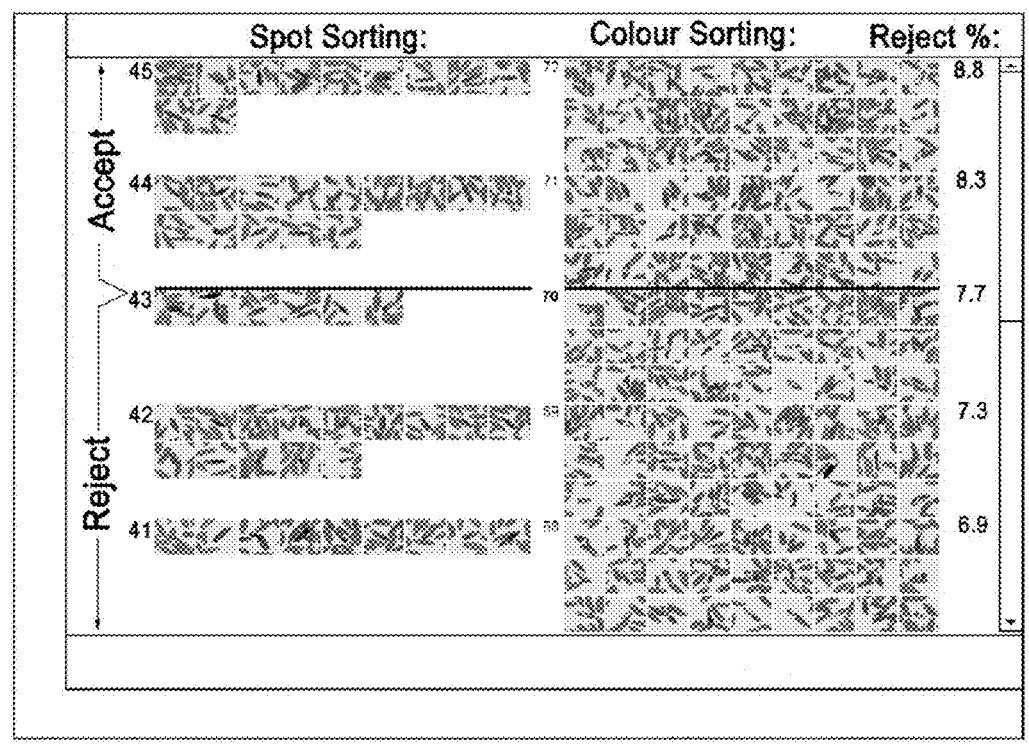
FIG. 8 shows a rearrangement of thumbnails from the same stream image as FIG. 7, but extended to include a second sorting criterion.

FIG. 8 illustrates the consequence of adding a second sorting criterion; in this case colour sorting. Each thumbnail is displayed in accordance with its ranking relative to the current sensitivity setting which is once again indicated as a bold horizontal line. Relative rank for a thumbnail within a sorting criterion is its rank relative to the current sensitivity of that criterion. A thumbnail is only displayed under one sorting criterion; namely, the criterion in which it has the lowest relative rank. As a consequence, many of the thumbnails shown in FIG. 7 under the spot sorting criterion do not appear. The reason for this is that thumbnails that are at one relative ranking under the spot sorting criterion, are at a lower relative ranking according to the colour sorting criterion. Thumbnails which appeared in the column under spot sorting have been transferred to the column covering colour sorting because of their lower relative ranking. In the special case that the lowest relative rank is shared by two sorting criteria then a priority rule is applied; ie, one criterion takes precedence over the other.

Because apparatus of the invention uses pixel colour to identify defects in colour sorting it can be readily adapted to show the boundary or edge of such defects. This information can be of considerable value.

As can be seen from FIGS. 7 and 8, the "current" sensitivity level for spot sorting is set at "43" whereas for colour sorting, the sensitivity level is set at "70". As shown, a thumbnail with a ranking of 44 according to the spot sorting criterion, and a ranking of 68 according to the colour sorting criterion will appear only in the colour sorting column where its relative ranking is lower.

On the righthand side of the display as shown in FIGS. 7 and 8, a percentage reject estimation is indicated according to the sensitivity setting or settings specified. As can be seen, it increases from 3% to 7.7% as a consequence of adding the colour sorting criterion. It will of course also alter if the sensitivity settings are adjusted, and this provides further useful information for the operator in determining what adjustments are to be made. A percentage reject can be provided against each row, and thus for a range of different machine configurations. The apparatus may also include a facility enabling the operator to disable the analysis under one or more of the defect criteria. This enables the operator to focus on one defect criterion or different combinations of criteria, and observe the virtual effect of altering the sensitivity level in those situations.

If the operator alters either or both of the sensitivity levels, then this will provoke movement of thumbnails from one column to the other. This is illustrated in FIGS. 10A and 10B on the basis of eighteen thumbnails whose lowest sensitivities are set out in the table of FIG. 9. In FIG. 10A, the sensitivity levels are those shown in FIG. 9 with the respective thumbnails in the spot sorting or colour sorting columns. What is seen on the screen of the interface is indicated in dotted outline. In FIG. 10B, the sensitivity level for spot sorting is increased from 43 to 45. The spot sorting column is lowered so that the current sensitivities for spot and colour sorting remain horizontally aligned, and it will be seen that thumbnail "J" in the colour sorting column of FIG. 10A, is now in the spot sorting column of FIG. 10B. The reason for this is that its relative rank is lower according to the spot sorting criterion when the sensitivity level for that criterion is increased.

Thumbnails for classification using the defect browser facility can also be graded by size and shape. This can be of different importance for different types of product to be sorted. Typical types of sorting by size are area, length and width. Typical types of sorting by shape are curvature (such as sharp angles and concavities), aspect ratios and circularity. In the case of size or shape sorting, articles can be displayed by their silhouette so the borders of the thumbnails are unnecessary and not displayed on the graphical user interface. FIG. 11 shows how two such criteria may be displayed on the graphical user interface.

For ease of explanation, the above description assumes that the computer processes the image data successively according to each of the defect criteria. However, in practice this will not be the case. Each identified defect will usually be processed individually on the basis of each of the defect criteria and ranked accordingly.

The above analysis is based on a situation in which thumbnails do not overlap. However, a thumbnail may contain more than one region of interest and therefore overlap with other thumbnails, as shown in FIG. 12. It is possible then to proceed on the basis that each thumbnail represents an individual article, and proceed as indicated above. However, this can result in the same defect being displayed more than once on the interface. Furthermore, the most severe defect may be just in a corner of the thumbnail, as illustrated in FIG. 13, with the consequence that the very part of the image that is triggering the identification of the thumbnail is not being clearly shown on the interface. In such a circumstance the thumbnail is not displayed on the basis that the severe defect will appear in another thumbnail.

The preferred method for handling overlapping thumbnails is to associate each thumbnail with the region of interest about which it is centred. The lowest sensitivity for each sorting criterion for that thumbnail is based on the detection of its associated region of interest as a defect. If a first thumbnail contains another region of interest then the thumbnail of this second region; the neighbouring thumbnail, is taken into consideration before displaying the first thumbnail. If the neighbouring thumbnail is associated with a region of interest that is a more severe defect than the region of interest of the first thumbnail, then the first thumbnail is not displayed on the interface.

The graphical user interface does of course present an electronic image that can be analysed. It also allows for focusing on individual images on display using a "zoom" facility to enlarge such an individual image or group of adjacent images.

The defect browser enables an operator to see at a glance, which defects are detected for a whole range of sensitivity settings. The ranking of the groups of thumbnails makes it easier to see the underlying ranking of the defects from severe to marginal rejects, and from marginal accepts to good product. This ranking can be easily seen, as can the consequence of any alteration of the sensitivity levels. The simultaneous display of the percentage reject estimate also informs the operator of the expected yield.

The defect browser also enables an operator to fine tune defect parameters that are not sensitivity settings, Whilst adjusting a defect parameter for a sorting criterion, the membership of the groups within the respective column on the graphical user interface changes. The parameters can thus be fine tuned until the arrangement of the groups of thumbnails in the column agrees with the intuition of the operator for ordering the thumbnails by severity of defect.

The defect browser also enables an operator to focus the display only on product classified for rejection, and ranked by severity of defect. This can be accomplished by scrolling the screen or merely blocking all images above the sensitivity levels. The advantage of this is that operators are likely to be more concerned with articles being rejected and by which sorting criteria.

Using the diagnostic facilities provided in the apparatus described provides guidance as to how a sorting machine can be adjusted to control quality and/or yield. Once virtual adjustments have been analysed and approved, they can be applied to the operating machine. Any changes made can of course be monitored subsequently using these facilities.

The invention claimed is:

1. Optical sorting machine comprising an inspection apparatus which comprises a feed system for delivering a stream of articles to an imaging zone; a camera for generating image data from said stream at the imaging zone; a graphical user interface configured to provide a display; a computer configured to process said image data, said computer comprising a pattern recognition system configured to identify defects in image areas from said image data and to rank the image areas in which the defects have been identified with respect to one another according to the severity of the identified defects for each of a plurality of defect criteria, and to provide a rank order of the image areas in which the defects have been identified with respect to each of said plurality of defect criteria, said computer being coupled to said graphical user interface and configured to display said image areas in which the defects have been identified as multiple thumbnails on the graphical user interface and to arrange said multiple thumbnails on said graphical user interface in said rank order for each of at least two of said plurality of defect criteria; wherein the computer is configured with a sensitivity level defining a qualifying ranking in each criterion of said plurality of defect criteria, and to display said multiple thumbnails in sequence with the qualifying rankings at the same level in the display on said graphical user interface; a sorting zone downstream of the imaging zone; and ejectors at the sorting zone to eject articles from said stream; wherein the plurality of defect criteria includes sorting criteria comprising at least two of spot sorting, colour sorting, size sorting and shape sorting; wherein the computer is configured to process image data from the camera and instruct the ejectors according to said sorting criteria; wherein the computer is configured to segment the image data to identify pixels which correspond to all articles in a section of said stream, and pixels which correspond with articles to be elected according to the sorting criteria; wherein the computer is configured to compare the numbers of said pixels to estimate the proportion of the stream of articles to be elected; and wherein the pattern recognition system comprises a colour classifier configured to identify pixels corresponding to potential defects in said stream of articles and a spatial filter configured to determine whether the identified pixels corresponding to potential defects warrant election of a respective article.

2. Optical sorting machine according to claim 1 wherein the computer is further configured to generate a visible image of said stream.

3. Optical sorting machine according to claim 1 wherein the pattern recognition system comprises a feature extractor configured to extract information from said image data; and a classifier configured to interpret said information.

4. Optical sorting machine according to claim 1 wherein one of the plurality of defect criteria is shape or size; and wherein the displayed multiple thumbnails each include a silhouette of the respective article.

5. Optical sorting machine according to claim 1 wherein the qualifying rankings are identified and visible on said graphical user interface during display of the multiple thumbnails.

6. Optical sorting machine according to claim 1 wherein said computer is configured to display only thumbnails with defects ranked below the qualifying rankings.

7. Optical sorting machine according to claim 1 wherein said computer is configured to display the thumbnail with a defect in more than one criterion only in the sequence in which the rank of the defect relative to its qualifying ranking is lower than it is in the at least one other criterion.

8. Optical sorting machine according to claim 1 wherein said computer is configured with at least one of said sensitivity levels being variable.

9. Optical sorting machine according to claim 1 wherein said computer is configured to define at least one of said image areas from the image data around each identified defect with said defect central therein.

10. Optical sorting machine according to claim 9 wherein the computer is configured such that said image areas with said defect central therein are defined even if parts of neighbouring image areas overlap in the image data.

11. Optical sorting machine according to claim 9 wherein the computer is configured to not include a thumbnail in the image displayed on the graphical user interface when a defect is within an image area in addition to that centrally therein and that additional defect is ranked at a lower level than the central defect.

12. Optical sorting machine according to claim 1 wherein the computer is configured to display on the graphical user interface images of articles not exhibiting defects.

13. Optical sorting machine according to claim 1 wherein the computer is configured to highlight pixels identified by the colour classifier on said graphical user interface.

14. Optical sorting machine according to claim 1 wherein the computer is configured to highlight identified pixels corresponding to potential defects that warrant ejection of respective articles on said graphical user interface.

15. A method of inspecting a stream of articles on an optical sorting machine comprising:
   a) delivering the stream of articles to an imaging zone;
   b) generating image data from the stream of articles at the imaging zone;
   c) processing the image data, said processing including:
      identifying defects in image areas from the image data by pattern recognition comprising:
         colour classification to identify pixels corresponding to potential defects in said stream of articles; and
         spatial filtering of the identified pixels corresponding to potential defects to determine whether a respective article warrants election; and
      ranking, according to severity of the identified defects, the image areas in which defects have been identified for each of a plurality of defect criteria, said ranking including providing a rank order of the image areas in which the defects have been identified with respect to each of the plurality of defect criteria, wherein said defect criteria include sorting criteria comprising at least two of spot sorting, colour sorting, size sorting and shape sorting;

d) defining a qualifying ranking in each criterion of said plurality of defect criteria by a sensitivity level in each criterion;
e) displaying said image areas in which the defects have been identified as multiple thumbnails, said displaying including arranging the multiple thumbnails in said rank order for each of at least two of said plurality of defect criteria, said displaying including arranging said multiple thumbnails in sequence with the qualifying rankings at the same level in the display;
(f) segmenting the image data to identify pixels which correspond to all articles in a section of said stream, and pixels which correspond with articles to be elected according to the sorting criteria; and comparing the numbers of said pixels to estimate the proportion of the stream of articles to be elected; and
(g) sorting downstream of the imaging zone and electing articles from said stream according to said sorting criteria.

* * * * *